(12) United States Patent
Suzuki et al.

(10) Patent No.: US 9,987,361 B1
(45) Date of Patent: Jun. 5, 2018

(54) COMPOSITIONS AND METHOD FOR SUSTAINED DRUG DELIVERY BY ACTIVE TRANSDERMAL TECHNOLOGY

(71) Applicant: Noven Pharmaceuticals, Inc., Miami, FL (US)

(72) Inventors: Masayuki Suzuki, Miami, FL (US); Cormac H. Lyons, Miami, FL (US)

(73) Assignee: NOVEN PHARMACEUTICALS, INC., Miami, FL (US)

( * ) Notice: Subject to any disclaimer, the term of this patent is extended or adjusted under 35 U.S.C. 154(b) by 0 days. days.

(21) Appl. No.: 14/974,782

(22) Filed: Dec. 18, 2015

Related U.S. Application Data

(60) Provisional application No. 62/097,320, filed on Dec. 29, 2014.

(51) Int. Cl.
| | | |
|---|---|---|
| A61K 47/28 | (2006.01) | |
| A61K 47/26 | (2006.01) | |
| A61K 47/10 | (2017.01) | |
| A61K 9/00 | (2006.01) | |
| A61K 31/27 | (2006.01) | |
| A61K 47/22 | (2006.01) | |
| A61K 9/70 | (2006.01) | |
| A61M 37/00 | (2006.01) | |

(52) U.S. Cl.
CPC ........... *A61K 47/28* (2013.01); *A61K 9/0021* (2013.01); *A61K 9/7023* (2013.01); *A61K 31/27* (2013.01); *A61K 47/10* (2013.01); *A61K 47/22* (2013.01); *A61K 47/26* (2013.01); *A61M 37/0015* (2013.01); *A61M 2037/0023* (2013.01); *A61M 2037/0061* (2013.01)

(58) Field of Classification Search
CPC .................................................. A61K 47/28
See application file for complete search history.

(56) References Cited

U.S. PATENT DOCUMENTS

| | | |
|---|---|---|
| 5,179,086 A | 1/1993 | Flender |
| 6,299,888 B1 | 10/2001 | Mizobuchi et al. |
| 6,512,010 B1 | 1/2003 | Gale et al. |
| 6,517,864 B1 | 2/2003 | Jacobsen et al. |
| 9,248,104 B2 | 2/2016 | Valia et al. |
| 2004/0258741 A1 | 12/2004 | Terahara et al. |
| 2009/0238860 A1 | 9/2009 | Saeki et al. |
| 2010/0266670 A1 | 10/2010 | Yamamoto et al. |
| 2011/0071204 A1 | 3/2011 | Takahashi et al. |
| 2013/0053357 A1 | 2/2013 | Kuma et al. |
| 2013/0053358 A1 | 2/2013 | Aida et al. |

FOREIGN PATENT DOCUMENTS

| | | | |
|---|---|---|---|
| JP | 11-005733 | 1/1999 | |
| JP | 2002-265346 A | 9/2002 | |
| JP | 2007/284378 A | 11/2007 | |
| WO | WO 02/19985 A2 * | 3/2002 | |
| WO | WO 0219985 A2 * | 3/2002 | ........... A61K 9/0021 |
| WO | WO 2008/044336 A1 | 4/2008 | |

OTHER PUBLICATIONS

U.S. Food and Drug Administration. "Select Committee on GRAS Substances (SCOGS) Opinion: Corn Sugar (Dextrose), Corn Syrup, Invert Sugar." (c) 1976. Available from: < http://www.fda.gov/Food/IngredientsPackagingLabeling/GRAS/SCOGS/ucm261263.htm >.*
U.S. Food and Drug Administration. "Inactive Ingredient Search for Approved Drug Products." (c) 2010. Available from: < http://www.accessdata.fda.gov/scripts/cder/iig/getiigWEB.cfm >.*
Elias, P.M., et al. "The Potential of Metabolic Interventions to Enhance Transdermal Drug Delivery." © 2002. The Society for Investigative Dermatology, Inc. pp. 79-85.*
Michels, A.J. Linus Pauling Institute. Oregon State University. "Vitamin E and Skin Health." © Feb. 2012. Available from: < http://lpi.oregonstate.edu/mic/health-disease/skin-health/vitamin-E >.*
Kasahara et al., "Carthami Flos Extract and its Component, Stigmasterol, Inhibit Tumour Promotion in Mouse Skin Two-Stage Carcinogensis," Phytotherapy Research, vol. 8, No. 6, pp. 327-331, 1994.
Kaminaga et al., "Inhibitory Effect of *Poria cocos* on 12-O-Tetradecanoylphorbol-13-Acetate-Induced Ear Oedema and Tumour Promotion in Mouse Skin," Phytotherapy Research, vol. 10, No. 7, pp. 581-584, 1996.
Yasukawa et al., "Inhibitory Effects of Sterols Isolated from *Chlorella vulgaris* on 12-O-Tetradecanoylphorbol-13-acetate-Induced Inflammation and Tumor Promotion in Mouse Skin," Biol. Pharm. Bull., vol. 19, No. 4, pp. 573-576, 1996.
Zhao et al., "Transdermal delivery of tolterodine by O-acylmenthol: In vitro/in vivo correlation," International Journal of Pharmaceutics, vol. 374, No. 1-2, pp. 73-81, Jun. 2009.
Elshafeey et al., "Utility of Nanosized Microemulsion for Transdermal Delivery of Tolterodine Tartrate: Ex-Vivo Permeation and In-Vivo Pharmacokinetic Studies," Pharmaceutical Research, vol. 26, No. 11, pp. 2446-2453, Nov. 21, 2009.
MC Chesney, "Preventing the contact dermatitis caused by a transdermal clonidine patch," The Western Journal of Medicine, vol. 154, No. 6, p. 736, Jun. 1991.
Koji et al., "Skin irritation in transdermal drug delivery systems: a strategy for its reduction," Pharmaceutical Research, vol. 24, No. 2, pp. 399-408, Feb. 2007.
Loden et al., "Effect of topically applied lipids on surfactant-irritated skin," British Journal of Dermatology, vol. 134, pp. 215-220, 1996.
Lopez-Castellano et al., "The Influence of Span® 20 on Stratum Corneum Lipids in Langmuir Monolayers: Comparison with Azone," International Journal of Pharmaceutics, vol. 203, pp. 245-253, 2000.

\* cited by examiner

*Primary Examiner* — Noble E Jarrell
*Assistant Examiner* — John S Kenyon
(74) *Attorney, Agent, or Firm* — Foley & Lardner LLP

(57) ABSTRACT

Described are compositions, methods and devices for providing sustained transdermal drug delivery using anti-healing compounds to prolong the effects of active transdermal technologies.

18 Claims, 4 Drawing Sheets

COMPOSITIONS AND METHOD FOR SUSTAINED DRUG DELIVERY BY ACTIVE TRANSDERMAL TECHNOLOGY

CROSS-REFERENCE TO RELATED PATENT APPLICATIONS

This application claims priority from Provisional Application U.S. Application 62/097,320, filed Dec. 29, 2014, incorporated herein by reference in its entirety.

FIELD

The present disclosure generally relates to the field of active transdermal technologies, such as microneedle technologies, and compositions and methods for achieving sustained drug delivery using active transdermal technologies.

BACKGROUND

Active transdermal technologies such as microneedle devices can expand the drugs that can be delivered transdermally to include small molecule drugs (e.g., drugs having a molecular weight greater than 500 Da) and biomolecules (e.g., peptides, proteins, and nucleic acids) by creating breaches in the stratum corneum that provide pathways for drug transport. However, the skin's healing mechanisms limit the duration of this effect, since the skin gradually recovers to an intact condition. Thus, the enhanced drug delivery made possible by active transdermal technologies such as microneedle devices is limited by the skin's healing processes, and gradually ceases as the skin heals. As a result, active transdermal technologies generally are not useful to achieve drug delivery over a sustained period of time.

Speaking generally, the skin healing mechanism is divided into three processes: inflammation, proliferation, and skin remodeling. See G. Broughton et al., "The Basic Science of Wound Healing," *Plastic and Reconstructive Surgery* 117(7 Suppl.): 12S-34S (June 2006); P. Ghosh et al., "Effect of formulation pH on transport of naltrexone species and pore closure in microneedle-enhanced transdermal drug delivery," *Molecular Pharm.* 10:2331-2339 (Jun. 3, 2013). Inhibiting these processes and extending the lifetime of open microchannels created by active transdermal technologies may prolong the time period during which enhanced drug delivery can be achieved. In this regard, some anti-inflammatory drugs, such as diclofenac, have been reported to extend the lifetime of microchannels. See N. K. Brogden et al., "Diclofenac delays micropore closure following microneedle treatment in human subjects," *J. Control Release* 163:220-229 (Aug. 21, 2012); N. K. Brogden et al., "Diclofenac Enables Unprecedented Week-Long Microneedle-Enhanced Delivery of a Skin Impermeable Medication in Humans," *Pharm. Res.* 30:1947-1955 (Aug. 1, 2013); P. Ghosh et al., "Optimization of Naltrexone Diclofenac Codrugs for Sustained Drug Delivery Across Microneedle-Treated Skin," *Pharm. Res.* 31:148-159 (January 2014). Also, HMG-CoA reductase inhibitors, such as fluvastatin, have been reported to extend the lifetime of microchannels. See P. Ghosh et al., "Fluvastatin as a Micropore Lifetime Enhancer for Sustained Delivery Across Microneedle-Treated Skin," *J. Pharm. Sci.* 103:652-660 (Jan. 6, 2014). However, the use of agents that themselves are active pharmaceutical ingredients (APIs) presents drawbacks due to their pharmaceutical activity and accompanying side effects, which limits their use to specific patient populations, and which may prevent their use in combination with other drugs.

Thus, there remains a need for compositions and methods for achieving sustained drug delivery using active transdermal technologies.

SUMMARY OF THE INVENTION

In accordance with some embodiments, there are provided methods of prolonging the transdermal delivery of a drug through the skin of a subject in need thereof, comprising treating a site of the subject's skin that has been or will be treated with an active transdermal device to form microchannels in the subject's skin at the skin site with an anti-healing compound that inhibits healing of the skin to close the microchannels. In specific embodiments, the anti-healing compound is not diclofenac or an HMG-CoA reductase inhibitor.

In accordance with some embodiments, there are provided methods of transdermally administering a drug through the skin of a subject in need thereof, comprising treating a site of the subject's skin with an active transdermal device to form microchannels in the subject's skin at the skin site; treating the skin site with an anti-healing compound that inhibits healing of the skin to close the microchannels; and transdermally administering the drug through the skin site. In specific embodiments, the anti-healing compound is not diclofenac or an HMG-CoA reductase inhibitor.

In embodiments where the anti-healing compound and drug are formulated in the same composition, the method may be effected by (a) treating the skin site with an active transdermal device and (b) before or after step (a), applying the composition comprising the anti-healing compound and drug to the skin site. In embodiments where the anti-healing compound and drug each are provided separately from the active transdermal device, the method may be is effected by (a) treating the skin site with the active transdermal device; (b) before or after step (a), applying a composition comprising the anti-healing compound to the skin site; and (c) after step (a) and before or after step (b), applying a composition comprising the drug to the skin site. In specific embodiments, the anti-healing compound is formulated in a solid, semi-solid, liquid, gel, ointment, cream, or emulsion composition formulated for transdermal administration; the drug is formulated in a polymer matrix composition formulated for transdermal administration, and step (b) is carried out prior to step (c).

In accordance with any of the methods or devices described herein, the anti-healing compound may be selected from the group consisting of compounds classified as Generally Recognized As Safe (GRAS) by the U.S. Food and Drug Administration (FDA) or listed on the Inactive Ingredient (IIG) list maintained by the FDA that inhibit the healing of the skin to close microchannels, or may be selected from the group consisting of cholesterol, tocopherol, curcumin, glycyrrhizin, butylated hydroxytoluene (BHT), butylated hydroxyanisole (BHA), ascorbic acid, sterols, squalene, ginsenoside, glutathione, N-acetylcysteine, catechin, quercetin, uric acid, bilirubin, glucose, flavonoids, ceramide, fatty acids (such as oleic acid, stearic acid, and palmitic acid), methylsilanol hydroxyproline aspartate, retinol acetate, L-ascorbyl palmitate, aluminium hydroxide, titanium(IV) oxide, sucrose esters of fatty acids, ethylenediaminetetraacetic acid (EDTA), pantethine, lecithin, derivatives thereof, analogs thereof, and mixtures of two or more thereof. In specific embodiments, the anti-healing compound is selected from the group consisting of cholesterol, tocopherol, and a mixture thereof, or is selected from anti-inflammatory compounds other than diclofenac, antioxidant compounds, and mixtures thereof.

In any of the methods described herein, the anti-healing compound may be applied in an amount effective to prolong the lifetime of the microchannels by at least 2 hours, or by at least 24 hours. 9.

In any of the methods described herein, the anti-healing compound and/or the drug may be formulated in a composition for transdermal administration, such as in a solid, semi-solid, liquid, gel, ointment, cream, or emulsion composition for transdermal administration.

In methods using an active transdermal device, the device may be a microneedle device comprising an array of a plurality of microneedles. In some embodiments, the anti-healing compound and/or the drug may be coated on and/or incorporated into the microneedles and/or a face of the microneedle device, such that one or all steps of the method is effected by applying the microneedle device to the skin site. In embodiments where the drug is coated on and/or incorporated into the microneedles and/or a face of the microneedle device, the method may be effected by (a) applying the microneedle device to the skin site, and, (b) before or after step (a), treating the skin site with the anti-healing compound. In embodiments where the anti-healing compound is coated on and/or incorporated into the microneedles and/or a face of the microneedle device, the method may be effected by (a) applying the microneedle device to the skin site, and, (b) before or after step (a), applying a transdermal composition comprising a drug.

In methods using an active transdermal device, the device may be selected from the group consisting of microneedle devices, radio frequency ablation devices, thermal ablation devices, chemical ablation devices, laser ablation devices, rubbing ablation devices, electroporation devices, jet injection devices, water jet devices, irradiation devices, and plasma treatment devices.

In accordance with some embodiments, there are provided active transdermal devices that form microchannels in a subject's skin having a skin-treatment side that contacts the skin during use, and comprising an anti-healing compound that inhibits healing of the skin to close the microchannels, and is coated on or incorporated into the skin-treatment side of the active transdermal device. In specific embodiments, the anti-healing compound is not diclofenac or an HMG-CoA reductase inhibitor. In some embodiments, the device is a microneedle device comprising an array of a plurality of microneedles, and the anti-healing compound and/or drug is coated on and/or incorporated into the microneedles and/or a face of the microneedle device. In some embodiments, the device includes an amount of the anti-healing compound effective to prolong the lifetime of the microchannels by at least 2 hours, or at least 24 hours.

In accordance with some embodiments, the device is configured to support a flexible, finite polymer matrix composition. In specific embodiments, the device is packaged with a flexible, finite polymer matrix composition comprising a drug.

Also provided are packaged combinations comprising (a) an active transdermal device that forms microchannels in a subject's skin having a skin-treatment side that contacts the skin during use, and comprising a drug coated on or incorporated into the skin-treatment side of the active transdermal device; and (b) a composition formulated for transdermal administration comprising an anti-healing compound that inhibits healing of the skin to close the microchannels; or (a) an active transdermal device that forms microchannels in a subject's skin; (b) a composition formulated for transdermal administration comprising an anti-healing compound that inhibits healing of the skin; and (c) a composition formulated for transdermal administration comprising a drug; or (a) an active transdermal device that forms microchannels in a subject's skin having a skin-treatment side that contacts the skin during use, comprising a composition formulated for transdermal administration comprising an anti-healing compound that inhibits healing of the skin to close the microchannels, wherein the composition is coated on or incorporated into the skin-treatment side of the active transdermal device; and (b) a composition formulated for transdermal administration comprising a drug. In specific embodiments, the anti-healing compound is not diclofenac or an HMG-CoA reductase inhibitor.

Also provided are anti-healing compounds as described herein that inhibits healing of skin to close microchannels formed in the skin by an active transdermal device, for use in prolonging the transdermal drug delivery of a drug through the skin of a subject in need thereof, and uses of anti-healing compounds as described herein that inhibit healing of skin to close microchannels formed in the skin by an active transdermal device, in the preparation of a medicament for prolonging the transdermal delivery of a drug through the skin. In specific embodiments, the anti-healing compound is not diclofenac or an HMG-CoA reductase inhibitor.

DETAILED DESCRIPTION

Figure 1:
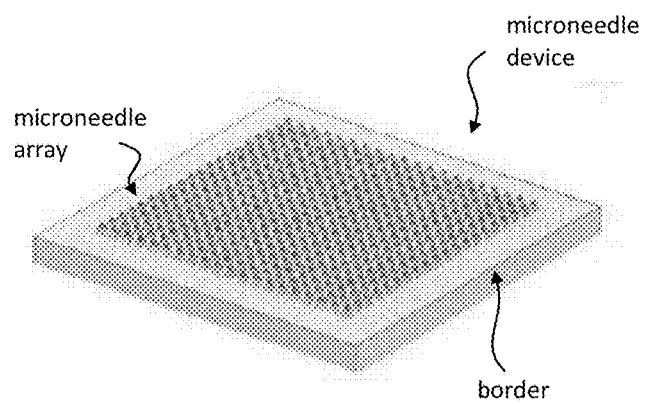
FIG. 1 is a front, top perspective view of a microneedle device that can be used in embodiments described herein.

Described herein are compositions, methods and devices for providing sustained transdermal drug delivery using anti-healing compounds to prolong the effects of active transdermal technologies.

Definitions

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The phrase "substantially free" as used herein generally means that the described material (e.g., transdermal drug delivery system, polymer, microneedle, etc.) comprises less than about 5%, less than about 3%, or less than about 1% by weight, based on the total weight of the material at issue, of the excluded component. The phrase "free of" as used herein means that the described material (e.g., polymer, microneedle, etc.) is formed without adding the excluded component(s) as an intended component, although trace amounts may be present, such as being a by-product or contaminant, such that the material comprises at most only trace amounts of the excluded component(s).

As used herein "subject" denotes any animal in need of drug therapy or biological fluid sampling, including humans. For example, a subject may be suffering from or at risk of developing a condition that can be treated or prevented with a drug, or may be taking a drug for health maintenance purposes, or may be having a biological fluid sample taken for diagnostic, therapeutic or health maintenance purposes.

As used herein, the phrases "therapeutically effective amount" and "therapeutic level" mean that drug dosage or plasma concentration in a subject, respectively, that provides the specific pharmacological response for which the drug is administered to a subject in need of such treatment, for whatever reason. It is emphasized that a therapeutically effective amount or therapeutic level of a drug will not always be effective in treating the target conditions/diseases, even though such dosage is deemed to be a therapeutically effective amount by those of skill in the art. For illustration only, exemplary dosages, drug delivery amounts, therapeutically effective amounts and therapeutic levels are provided below with reference to adult human subjects. Those skilled in the art can adjust such amounts in accordance with standard practices as needed to treat a specific subject and/or condition/disease.

As used herein "active transdermal technologies" refers to transdermal technologies that involve the creation of breaches in the skin that provide pathways for drug transport, referred to herein as "microchannels." Examples of active transdermal technologies include microneedles, electroporation (the use of short electrical pulses of high voltage to create pores in the skin), sonophoresis (the use of low-frequency ultrasonic energy to disrupt the stratum corneum), radio frequency ablation, thermal ablation, chemical ablation, laser ablation, rubbing ablation, water jet technology, irradiation, or plasma treatment. Thus, an "active transdermal device" may be a microneedle device comprising an array of a plurality of microneedles, a radio frequency ablation device, a thermal ablation device, a chemical ablation device, a laser ablation device, an electroporation device, a jet injection device, a water jet device, an irradiation device, a plasma treatment device, or any other device capable of creating microchannels in the skin that provide pathways for drug transport. For the sake of convenience, the description below discusses the compositions and methods disclosed herein with reference to microneedle devices, but is should be understood that the compositions and methods can be used in conjunction with any active transdermal technology that involves the creation of microchannels in the skin that provide pathways for drug transport.

In the following description, for purposes of explanation and not limitation, details and specific embodiments are set forth in order to provide a thorough understanding of the invention. It will be apparent to those skilled in the art that the invention may be practiced in other embodiments that depart from the details and specific embodiments Anti-Healing Compounds Described herein are compositions, methods and devices that use anti-healing compounds to prolong the effects of active transdermal technologies by prolonging the lifetime of microchannels created in the skin by an active transdermal technology. In some embodiments the anti-healing compounds are GRAS compounds, e.g., compounds that are classified as Generally Recognized As Safe by the U.S. Food and Drug Administration (FDA), in accordance with sections 201(s) and 409 of the Federal Food, Drug, and Cosmetic Act (the Act), and the implementing regulations. In some embodiments the anti-healing compounds are not active pharmaceutical ingredients, e.g., they are not compounds that have been approved as drugs by the FDA and/or they are listed on the Inactive Ingredient (IIG) list maintained by the FDA. In other embodiments the anti-healing compounds are compounds whose safety profile is well-understood and established. As used herein, the term "GRAS anti-healing compounds" does not include diclofenac or HMG-CoA reductase inhibitors, such as fluvastatin. In some embodiments the anti-healing compounds have an anti-inflammatory effect. In some embodiments the anti-healing compounds are antioxidant compounds. In some embodiments, the anti-healing compounds do not include diclofenac or HMG-CoA reductase inhibitors, such as fluvastatin.

In particular, the inventors have determined that the following compounds are useful as anti-healing compounds: cholesterol, tocopherol, curcumin, glycyrrhizin, butylated hydroxytoluene (BHT), butylated hydroxyanisole (BHA), ascorbic acid, sterols, squalane, squalene, ginsenoside, glutathione, N-acetylcysteine, catechin, quercetin, uric acid, bilirubin, glucose, flavonoids, ceramide, fatty acids (such as oleic acid, stearic acid, and palmitic acid), methylsilanol hydroxyproline aspartate, retinol acetate, L-ascorbyl palmitate, aluminium hydroxide, titanium(IV) oxide, sucrose esters of fatty acids, ethylenediaminetetraacetic acid (EDTA), pantethine, and lecithin. Thus, in some embodiments an anti-healing composition includes one or more of these compounds, derivatives thereof, and/or analogs thereof. In specific embodiments, an anti-healing composition comprises one or more of cholesterol and tocopherol, and/or derivatives and/or analogs thereof. Examples of derivatives and analogs of cholesterol that may be used include 25-OH cholesterol, 22,25-diazacholesterol, 20,25-diazacholesterol, 25-hydroxycholesterol, cholesterol esters, cholesterol sulfate, cholesterol oleate, cholesteryl palmitate, cholesteryl stearate, cholesterol phosphate, cortisol, calcitriol, ergocalciferol, cholecalciferol, thiocholesterol, 6-ketocholestanol, cholesteryl acetate, bile acid, coprostane, lanosterol, thiocholesterol, campesterol, calcipotriol, tacalcitol, β-sitosterol, α-spinasterol, and ergosterol. Examples of derivatives and analogs of tocopherol that may be used include tocopherol acetate, tocopherol nicotinate, tocotrienol, and tocopheryl acid succinate. Examples of derivatives and analogs of ascorbic acid that may be used include ascorbyl-2-phosphate and ascorbic acid 2-glucoside. Examples of derivatives and analogs of curcumin that may be used include tetrahydrocurcumin, curcumen, and didemethoxycurcumin. Examples of derivatives and analogs of glycyrrhizin that may be used include glyyrrhetinic acid, stearylglycyrrhetinate, ammonium glycyrrhizinate, and dipotassium glycyrrhizate. In further specific embodiments, an anti-healing composition comprises cholesterol and tocopherol, and/or derivatives and/or analogs thereof. In some embodiments, an anti-healing composition does not include diclofenac or an HMG-CoA reductase inhibitor, such as fluvastatin.

Thus, in some embodiments, an anti-healing composition is provided that includes one or more anti-healing compounds in an amount effective to prolong the lifetime of a microchannel created by an active transdermal technology, such as a microchannel created by a microneedle device. The viability and lifetime of microchannels created by an active transdermal technology can be assessed by methodologies known in the art and illustrated in the examples below, such as by assessing transepidermal water loss, in vivo impedance, in vitro drug delivery, or in vivo pharmacokinetic parameters such as drug plasma concentration. As used herein, the phrase "amount effective to prolong the lifetime of a microchannel" means an amount effective to prolong the lifetime of a microchannel as assessed by any one or more of these parameters, e.g., an amount effective to increase transepidermal water loss, in vivo impedance, in vitro drug delivery, or drug plasma concentration for a longer period of time than is observed in a comparable method without the use of the compound. As used herein, a "longer period of time" includes 1 hour, 2 hours, 4 hours, 6 hours, 8 hours, 10 hours, 12 hours, 15, hours, 18 hours, 24 hours, 28 hours, 32 hours, 36 hours, 48 hours, 60 hours, 72 hours, or longer.

As discussed in more detail below, the anti-healing composition may be in any form suitable for use in a transdermal context, such as in solid (including powder), semi-solid, liquid, gel, ointment, cream, emulsion, or polymeric matrix (such as a flexible, finite polymer matrix, e.g., a "patch") form. As also discussed in more detail below, the anti-healing composition may be incorporated into the active transdermal device, such as being incorporated into the microneedle device material, may be applied to a skin-contacting portion of the active transdermal device, such as being applied to an exterior surface of the microneedles of a microneedle device or other skin-contacting surface, applied to a non-skin-contacting portion of the active transdermal device, or applied to the subject's skin separately, such as before or after application of the microneedle device. In any of these embodiments, the anti-healing composition may be separate from the composition comprising the drug(s) to be delivered, or the anti-healing compound and drug(s) may be formulated in the same composition.

Microneedle Devices

As noted above, anti-healing compositions described herein may be used in conjunction with active transdermal technologies, such as microneedle devices. Microneedle devices are known in the art, and the invention can be used in conjunction with any microneedle device. Examples of microneedle devices include devices with solid microneedle arrays (e.g., silicon or metal solid microneedle arrays), hollow microneedle arrays (e.g., silicon, metal, or glass hollow microneedle arrays), and semihollow microneedle arrays. Other examples include devices with polymer and hydrogel microneedle arrays, which may be dissolvable, swellable, and/or biodegradable. Further examples of microneedle devices that may be used include those with stainless steel microneedle arrays (such as those described in U.S. Pat. No. 7,712,198) and polylactic acid microneedle arrays (such as those described in U.S. Pat. No. 8,696,638). While specific embodiments of microneedle devices are described in more detail below, it should be understood that the invention is not limited to any specific type of active transdermal technology or microneedle device.

In one embodiment, a microneedle device may comprise an array of a plurality of microneedles, which may be disposed on a backing member. The backing member may be integrally formed with the microneedles and may be comprised of the same material as the microneedles. Additionally or alternatively, the backing member may be formed from any other material suitable for such purposes. In some embodiments, the backing member is flexible. In some embodiments, the backing member is in the form of a solid sheet or platform, such as a sheet (e.g., layer) comprising a suitable material, such as polyvinylpyrrolidone (PVP), polyvinylalchol, pullulan, chitosan, gelatin, sodium alginate, cellulose, polyacrylamide, poly(N-isopropylacrylamide) or its copolymers, hydroxypropylcellulose, hydroxypropylmethylcellulose, hydroxyethylcellulose, carboxymethylcellulose, silk polymer, amylopectin, chondroitin sulfate, poly (lactic-co-glycolic acid), poly-L-lactide, fibrin, elastin, collagen, hyaluronic acid, dextran, functionalized or modified species of the above, or mixtures or blends of two or more of the above. In other embodiments the backing member is in the form of a membrane, such as a flexible mesh membrane comprised of any suitable material, such as a flexible mesh membrane comprising nylon, polypropylene, stainless steel, ethylene-vinyl acetate, polyethylene terephthalate, polyurethane, woven or non-woven fabric, or combinations, mixtures or blends of two or more thereof.

In embodiments where the backing member is not integrally formed with the microneedles, the microneedle array may be applied to the backing member by any means known in the art, such as by using an adhesive material to adhere the microneedle array to the backing member or by heat-sealing the microneedle array to the backing member In accordance with any of the embodiments of microneedles and backing members described herein, the array of microneedles may be disposed on the backing member such that there is a peripheral border region on the backing member that does not comprise microneedles. The border may extend along the entire circumference of the backing member, or may be only on one or more portions thereof, such as one or more sides (or portions thereof) of a polygon-shaped backing member or one or more arcs of a round (e.g., circular or oval) backing member.

In specific embodiments, at least a portion of a border is provided with an adhesive to adhere the microneedle device to the skin surface during use. The adhesive may comprise any adhesive suitable for such use. In specific embodiments, the adhesive is a pressure-sensitive adhesive. In some embodiments, the entire border is provided with an adhesive. In other embodiments, only a portion of the border is provided with an adhesive. As used herein, the term "pressure-sensitive adhesive" refers to a viscoelastic material which adheres instantaneously to most substrates with the application of very slight pressure and remains tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives.

In any embodiments with an adhesive, the microneedle device may further comprise a removable release layer over the adhesive. When present, the release liner is removed from the device prior to use to expose the adhesive prior to application of the device. Materials suitable for use as release liners are well-known known in the art.

Figure 2A:
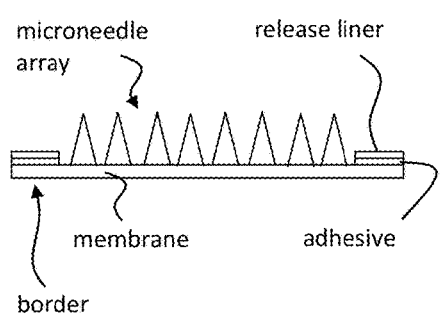
FIG. 2A is a side, cross-sectional view of a second microneedle device that can be used in embodiments described herein.
Figure 2B:
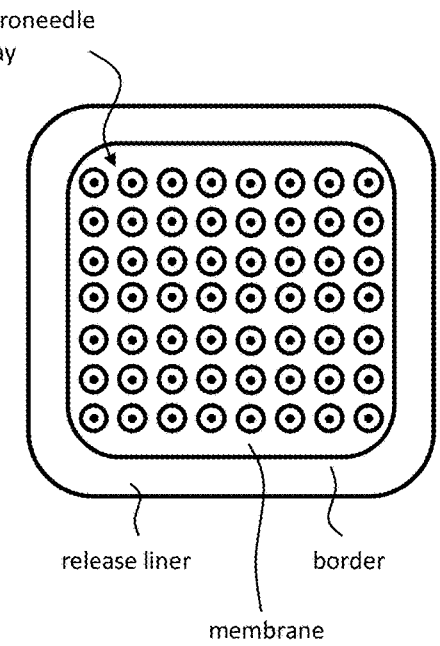
FIG. 2B is a top view of the microneedle device depicted in FIG. 2A.

Turning to the figures, FIG. 1 is a front, top perspective view of a microneedle device that may be used as described herein. The microneedle device includes an array of a plurality of microneedles disposed on a backing member (also referred to as a "basement"). As depicted in FIG. 1, the backing member could be formed integrally with the microneedle array or could be made of a different material, such as a material that is more flexible than the microneedle array. In another embodiment, shown in FIGS. 2A and 2B, the backing member is in the form of a flexible membrane, such as a flexible mesh membrane, such as a membrane made of, for example, nylon, polypropylene, or stainless steel. In the embodiments shown in FIGS. 1, 2A, and 2B, the backing member of the microneedle device includes a border extending peripherally around the microneedle array. As noted above and illustrated in FIGS. 2A and 2B, in some embodiments the border is provided with an adhesive to adhere the microneedle device to the skin surface during use, and a release liner covering the adhesive prior to use. The adhesive and release liner may be applied before or after irradiation of the microneedles.

A typical microneedle array may include from tens to several hundred microneedle projections per square centimeter. For example, a microneedle array may include 10 or more microneedles, 100 or more, or 1000 or more microneedles, including from about 50 to about 1000 per square centimeter, such as 200, 400, 500 or 900 microneedles per square centimeter. The dimensions of the microneedle can be selected and adjusted depending on the intended use (e.g., drug delivery or sampling). Typically, microneedles have a cone or square pyramid shape. Typically, microneedles have a length of from about 100 to about 1000 µm, including a length of about 200, 400 or 600 µm. Typically, microneedles have a base diameter of from about 100 to about 00 µm, including a base diameter of from about 120 to about 300 µm, such as a base diameter of about 120 µm or about 300 µm. A typical tip angle may be, for example, in a range of 10° to 45°, for example 34°. The needle-to-needle spacing per square centimeter can be selected and adjusted depending on the intended use (e.g., drug delivery or sampling, and specific drug(s) being delivered or material(s) being sampled). Typically, a microneedle array may have a needle-to-needle spacing per square centimeter of from about 50 to about 1000 µm, including from about 200 µm to about 400 µm. The spacing may be uniform or varied across the surface of the array. Typically, a microneedle may have an aspect ratio (ratio of microneedle length to base diameter) of from 0.5 to 3, including an aspect ratio of about 1.67. A typical device may have a needle density of 30%.

Devices Integrating Anti-Healing Compounds and/or Drugs

As noted above, the anti-healing compound or composition may be incorporated into an active transdermal device, provided on a surface of an active transdermal device, or provided separately for direct application to the subject's skin. For example, when the active transdermal device is a microneedle device, the anti-healing compound may be incorporated into and/or coated onto the microneedles and/or a face of the microneedle device.

When the anti-healing compound is incorporated into a skin-contacting material of the active transdermal device, it may be formulated in the solution of material that is used to form a skin-contacting surface of the active transdermal device. For example, when the active transdermal device is a microneedle device, the anti-healing compound may be formulated in the solution of material that is used to form an intermediate microneedle array structure, before setting.

Additionally or alternatively, the anti-healing compound may be provided in a component, composition, coating, or layer provided on a skin-treating side of the active transdermal device. For example, when the active transdermal device is a microneedle device, the anti-healing compound may be provided in a component, composition, coating, or layer provided on one or more of an exterior or interior surface of the microneedles and/or on at least one surface of the device (e.g., the "front" face from which the microneedles protrude into the skin and/or the opposite "back" face), such as any composition described in more detail below. In some embodiments, the anti-healing compound is applied to the active transdermal device during the manufacturing process, such that the final product contains the anti-healing compound. In other embodiments, the anti-healing compound is applied to the active transdermal device at the time of use. In accordance with the latter embodiments, the active transdermal device and anti-healing compound or composition may be provided in separate packages (optionally packaged together) with instructions to apply the anti-healing compound or composition to the active transdermal device prior to use.

In some embodiments, an anti-healing compound may be both incorporated in the material of the active transdermal device (e.g., microneedles) and provided separately, such as applied to a surface of a skin-contacting side of the active transdermal device (e.g., one or more of an exterior or interior surface of the microneedles and/or on a face of the microneedle device), and/or as a separate component or composition. In such embodiments, the same or different anti-healing compound(s) may be used in the material of the device and elsewhere, and the anti-healing compound(s) may be formulated in the same or different compositions, in the same or different form, and any permutation or combination thereof.

In specific embodiments, the anti-healing compound is provided in a flexible, finite transdermal drug delivery system (e.g., in a transdermal drug delivery patch) disposed on the skin after pretreatment with the active transdermal device.

When the active transdermal device is a microneedle device, the anti-healing compound may be provided in a flexible, finite transdermal drug delivery system (e.g., in a transdermal drug delivery patch) disposed on a face of a microneedle device, such as patch disposed on the back face of the microneedle device, such as on the back face of the backing member. In accordance with some embodiments, the microneedle device is configured to support the patch, such as by having dimensions suitable for supporting the patch. In some embodiments, the microneedle device and patch may be provided in separate packages (optionally packaged together) with instructions to remove the release liner from the patch and apply it to the back face of the microneedle device.

In other specific embodiments, the anti-healing compound is provided in a composition (e.g., in a transdermal delivery composition) that is provided on the skin-treatment side of the active transdermal device (e.g., one or more of an exterior or interior surface of the microneedles and/or on applied to a face of the microneedle device, such as a composition applied to the back face of the microneedle device, such as on the back face of the backing member). The anti-healing composition may be a solid (including powder), semi-solid, liquid, gel, ointment, cream, emulsion, or polymeric matrix composition that is applied to the skin-treatment side of the active transdermal device (e.g., one or more of an exterior or interior surface of the microneedles and/or on at least one face of the backing member). In any of these embodiments, the anti-healing compound may be formulated in any suitable form, including being dissolved, dispersed or suspended in a composition. In embodiments where the compound is in solid form, the compound may be in any solid form, including any crystalline or amorphous form, and/or provided as a particles (e.g., encapsulated particles, coated particles, nanoparticles, etc.).

In some embodiments where an anti-healing composition is applied to a back face of a microneedle device, the composition may be provided with a covering material that, together with the microneedle device, defines a cavity that contains the composition In such embodiments, the covering material and composition together may be referred to as a "patch" although the "patch" may be formed at the time of use. See, e.g., FIG. 3. In accordance with any of these embodiments, the microneedle device and composition may be provided in separate packages (optionally packaged together) with instructions to apply the composition to the microneedle device and, optionally, cover it with a covering material. In some embodiments, the composition is provided in a unit dose package (such as a packet or pre-filled syringe) or in a unit dose pump.

The drug(s) to be delivered can be provided in any manner described above for the anti-healing compound. In any of these embodiments, the anti-healing compound or composition may be separate from the drug(s) or drug(s)-containing composition, or the anti-healing compound and drug(s) may be formulated in the same composition. For example, the drug(s) and the anti-healing compound both may be incorporated into the microneedle material, may be applied to the same or different surfaces of the device, and/or may be applied directly to the subject's skin in the same or separate compositions. Further, the drug(s) and the anti-healing compound may be pre-mixed, mixed at the time of use, or applied separately to the active transdermal device and/or the skin of the subject. In some embodiments, the drug(s) and/or anti-healing compound may be provided in a separate transdermal delivery device, such as an iontophoresis device, a sonophoresis device, a magnetphoresis device, etc. In accordance with those embodiments, the active transdermal device may be employed prior to the drug and/or anti-healing compound delivery device, or they may be used together, such as by applying or attaching the separate transdermal delivery device to the active transdermal device.

Figure 3:
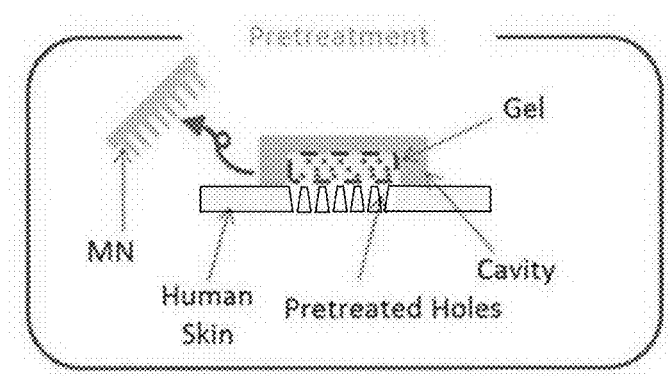
FIG. 3 is a side, cross-sectional view depicting a pretreatment method using a microneedle device that can be used in embodiments described herein.

Turning again to the figures, FIG. 3 illustrates a pretreatment method using a microneedle device. The microneedle device is applied to the skin to create microchannels ("pretreated holes") in the skin. Then, a patch-type transdermal drug delivery system is disposed on the skin at the pretreatment site. As shown in the figure and discussed above, the patch may include a cavity that holds a composition containing the an anti-healing compound and drug, such as a semi-solid, liquid, gel, ointment or emulsion formulation of the anti-healing compound and drug. Additionally or alternatively, an anti-healing composition may be applied directly to the subject's skin before or after the microneedle treatment. In such embodiments, the patch composition includes the drug to be delivered and optionally includes an additional amount of anti-healing compound, although in some embodiments the patch composition does not include the anti-healing compound. In the uses illustrated in FIG. 3, the microneedles pierce the skin, facilitating transdermal drug delivery from the device into the skin, while the anti-healing compound inhibits healing of the skin, thus prolonging the lifetime of the microchannels, and permitting sustained delivery of the drug.

Methods for Sustained Transdermal Drug Delivery

The compositions and devices described above are useful in methods for transdermal drug delivery, including methods for sustained transdermal drug delivery. The methods generally include treating the skin of the subject with an active transdermal device to create microchannels in the skin, treating the skin of the subject with an anti-healing compound that inhibits healing of the skin and prolongs the lifetime of the microchannels, and transdermally administering the drug to the subject. These steps can be effected simultaneously and sequentially in different orders, as illustrated below.

Simultaneous Embodiments

In some embodiments, the creation of microchannels, treatment with an anti-healing compound and transdermal administration of drug are effected substantially simultaneously, using an active transdermal device having a skin-treatment side that contacts the skin during use, wherein the anti-healing compound and drug are both coated on or incorporated into the skin-treatment side of the active transdermal device. For example, when the active transdermal device is a microneedle device and the anti-healing compound and drug are both coated on and/or incorporated into the microneedles and/or a face of the microneedle device, then applying the microneedles to the skin of the subject will result in the formation of microchannels, treatment with an anti-healing compound and transdermal administration of the drug. As noted above, the anti-healing compound and drug may be provided separately or together. For example, the anti-healing compound may be coated on the microneedles, and the drug may be incorporated into the microneedles and/or a face of the microneedle device, or may be provided in a flexible, finite transdermal drug delivery system (e.g., in a transdermal drug delivery patch) disposed on a face of a microneedle device, such as patch disposed on the back face of the microneedle device, such as on the back face of the backing member.

In some embodiments, the creation of microchannels and treatment with an anti-healing compound are effected substantially simultaneously, while the transdermal administration of drug is effected subsequently. In such embodiments, the active transdermal device is a device having a skin-treatment side that contacts the skin during use, and the anti-healing compound is coated on or incorporated into the skin-treatment side of the active transdermal device, while the drug is provided separately. For example, when the active transdermal device is a microneedle device, the anti-healing compound may be coated on and/or incorporated into the microneedles and/or a face of the microneedle device. The drug may be provided separately in any composition suitable for transdermal administration, including a solid (including powder), semi-solid, liquid, gel, ointment, cream, emulsion, or polymeric matrix composition (e.g., transdermal patch). In such embodiments, applying the microneedles to the skin of the subject will result in the formation of microchannels and treatment with an anti-healing compound. Then, the step of administering the drug to the subject is performed by applying the drug or drug-containing composition to the skin. For example, a patch-type transdermal drug delivery system, such as that shown in FIG. 3, may be disposed on the skin at the pre-treatment site.

In some embodiments, the creation of microchannels is effected first, followed by treatment with an anti-healing compound and transdermal administration of drug effected substantially simultaneously, such as in embodiments where the drug and anti-healing compound formulated together in the same composition. For example, the skin may be pre-treated with the active transdermal device, such as a microneedle device, a radio frequency ablation device, a thermal ablation device, a chemical ablation device, a laser ablation device, a rubbing ablation device, an electroporation device, a jet injection device, a water jet device, an irradiation device, or a plasma treatment device, resulting in the formation of microchannels. Then, a transdermal composition comprising the anti-healing compound and drug is applied to the pre-treated skin. The transdermal composition may be any composition suitable for transdermal administration, including a solid (including powder), semi-solid, liquid, gel, ointment, cream, emulsion, or polymeric matrix composition (e.g., transdermal patch). As noted above, FIG. 3 illustrates such embodiments, where the anti-healing compound and drug both are formulated in the "gel".

In some embodiments, the creation of microchannels is effected substantially simultaneously with the transdermal drug delivery, while treatment with the anti-healing compound is effected separately. For example, the active transdermal device may be a device having a skin-treatment side that contacts the skin during use, wherein the drug is coated on or incorporated into the skin-treatment side of the active transdermal device. For example, when the active transdermal device is a microneedle device comprising an array of a plurality of microneedles, the drug may be coated on and/or incorporated into the microneedles and/or a face of the microneedle device. In these embodiments, the anti-healing compound or composition typically is applied to the subject's skin first. For example, the anti-healing compound may be formulated in any composition suitable for transdermal administration, including a solid (including powder), semi-solid, liquid, gel, ointment, cream, emulsion, or polymeric matrix composition (e.g., transdermal patch), and applied to the subject's skin before treatment with the active transdermal device. Then, application of the active transdermal device results in the creation of microchannels and transdermal administration of the drug.

Separate Embodiments

In some embodiments, the creation of microchannels, treatment with an anti-healing compound and transdermal administration of drug each are effected in separate, sequential steps. For example, the skin may be treated with the anti-healing compound or composition applying the compound or composition directly to the skin, before or after treatment with the active transdermal device to create microchannels. As noted above, the active transdermal device may be any device that results in the formation of microchannels, such as a microneedle device, a radio frequency ablation device, a thermal ablation device, a chemical ablation device, a laser ablation device, a rubbing ablation device, an electroporation device, a jet injection device, a water jet device, an irradiation device, or a plasma treatment device. Then, transdermal administration of drug is effected by applying the drug to the skin. In these embodiments, the anti-healing compound and drug may be formulated in any composition suitable for transdermal administration, including a solid (including powder), semi-solid, liquid, gel, ointment, cream, emulsion, or polymeric matrix composition (e.g., transdermal patch), and may be formulated in the same type or different types of compositions. In specific embodiments, the anti-healing compound is formulated in semi-solid, liquid, gel, ointment, cream, or emulsion composition, while the drug is formulated in a polymeric composition (e.g., a transdermal patch) formulated for sustained drug delivery. FIG. 3 illustrates such embodiments, where the anti-healing compound is applied first (not pictured) and the drug is formulated in the "gel".

EXAMPLES

Example 1—In Vivo TEWL

This example shows the ability of (i) cholesterol, (ii) curcumin, and (iii) glycyrrhizin to prolong the lifetime of microchannels in skin made by a microneedle device, as measured by transepidermal water loss (TEWL).

Transepidermal water loss (TEWL) was assessed in vivo in swine as an indicator of skin integrity before and after microneedle pretreatment, using dipropylene glycol (DPG) formulated with saturated (i) cholesterol, (ii) curcumin, (iii) glycyrrhizin, (iv) diclofenac, or (v) no anti-healing compound. The diclofenac formulation was used as a positive control, and the formulation with no anti-healing compound was used as a negative control. Microneedle devices were inserted into swine skin with an applicator and removed, followed by application of the formulations. TEWL was measured before and after microneedle pretreatment, and during application of the formulations (formulations were removed and reapplied at every time point).

Figure 4:
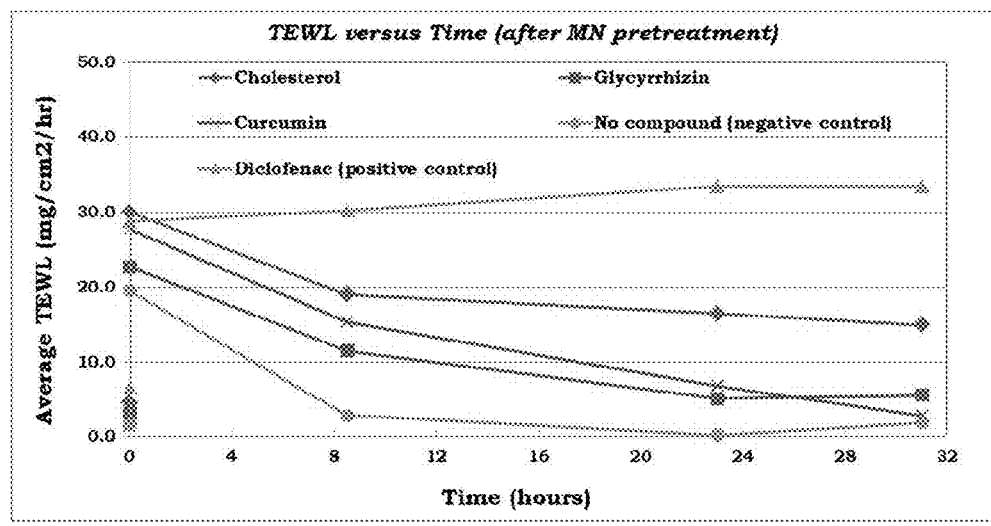
FIG. 4 illustrates the in vivo transepidermal water loss measured before and after pretreatment with dipropylene glycol (DPG) compositions formulated with cholesterol, curcumin, glycyrrhizin, diclofenac (positive control) or no anti-healing compound (negative control).

FIG. 4 illustrates the in vivo transepidermal water loss measured before and after microneedle pretreatment for the five formulations. While the diclofenac formulation yielded the highest sustained level of TEWL, the cholesterol, curcumin, and glycyrrhizin formulations all yielded higher sustained levels of TEWL than the formulation with no anti-healing compound.

Example 2—In Vivo Impedance

This example shows the ability of (i) cholesterol, (ii) curcumin, and (iii) glycyrrhizin to prolong the lifetime of microchannels in skin made by a microneedle device, as measured by impedance.

Impedance (Z) was assessed in vivo in swine as a measure of skin integrity using the compositions described above. Microneedle devices were inserted into swine with an applicator and removed, followed by application of the formulations. Impedance was measured before and after microneedle pretreatment, and during application of the formulations (formulations were removed and reapplied at every time point).

Figure 5:
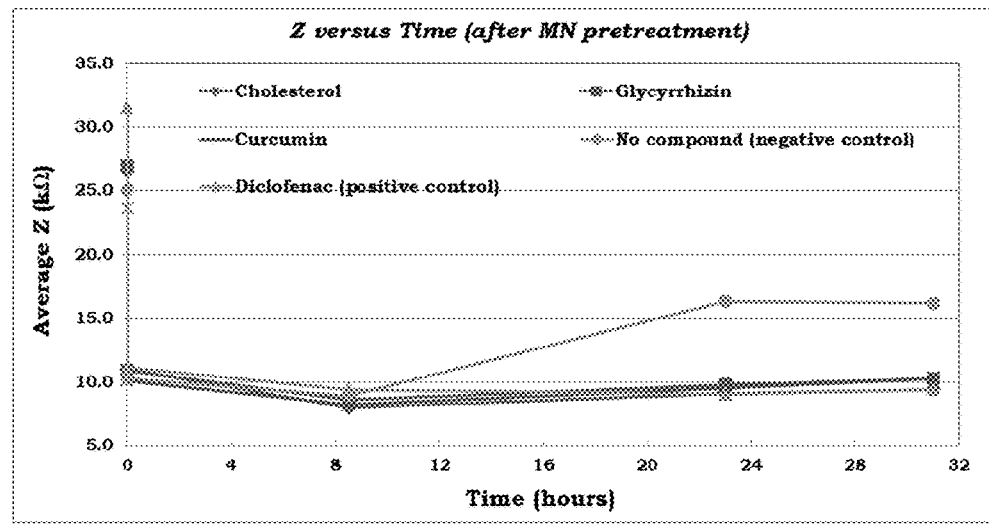
FIG. 5 illustrates the in vivo impedance measured before and after pretreatment with cholesterol, curcumin, or glycyrrhizin, using diclofenac as a positive control and a DPG composition as a negative control.

FIG. 5 illustrates the in vivo impedance measured before and after microneedle pretreatment for the five formulations. The diclofenac, cholesterol, curcumin, and glycyrrhizin formulation all yielded a low impedance throughout the study, while the impedance of the formulation with no anti-healing compound gradually increased.

Example 3—In Vitro Drug Delivery

This example shows that compositions formulated with cholesterol exhibit sustained drug delivery, as measured by in vitro drug flux through human cadaver skin.

Drug delivery through the skin was assessed in vitro using human cadaver skin samples in a modified Franz-diffusion cell experiment, using a composition comprising rivastigmine tartrate (3.4%) formulated in DPG (82.3%) and HPC (12.6%) (hydroxyl propyl cellulose) with cholesterol (1.7%). A microneedle device was inserted into human cadaver skin and removed, followed by application of the formulation. The Franz cell receiver compartment was periodically assayed for rivastigmine.

Figure 6:
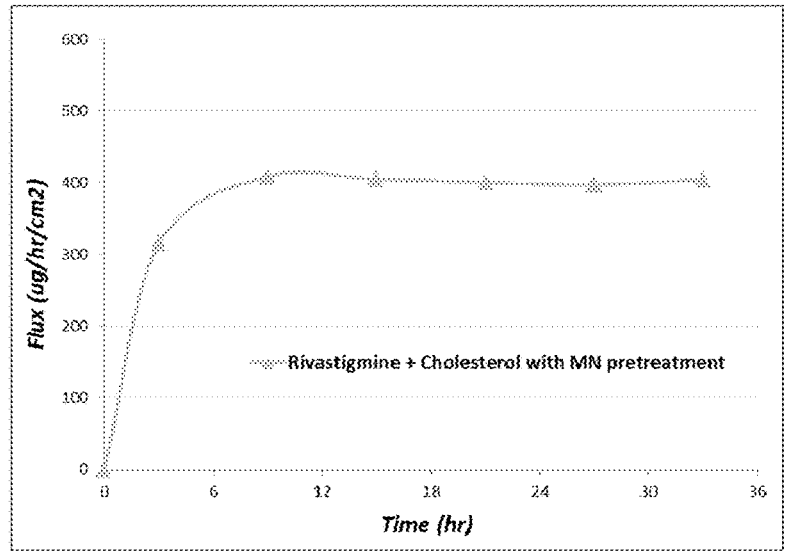
FIG. 6 illustrates the in vitro drug flux through the skin of rivastigmine using cholesterol as an anti-healing compound, when tested using a modified Franz-diffusion type cell set-up.

FIG. 6 illustrates the in vitro drug flux through the skin of rivastigmine from the cholesterol-containing composition. The data show that the cholesterol formulation exhibited sustained drug delivery over the time period studied.

Example 4—In Vivo Drug Delivery

This example shows the ability of cholesterol to enhance in vivo drug delivery, as measured by drug plasma concentration in swine.

Plasma levels of rivastigmine were assessed in vivo in swine using rivastigmine gel patch compositions formulated with cholesterol, diclofenac, or no anti-healing compound. The cholesterol composition included 3.4% rivastigmine, 82.3% DPG, 12.6% HPC, and 1.7% cholesterol. The diclofenac composition included 3.4% rivastigmine, 80.6% DPG, 12.6% HPC, and 3.4% diclofenac. The gel with no anti-healing compound included 3.4% rivastigmine, 84% DPG, and 12.6% HPC. A microneedle device was inserted into the skin and removed, followed by application of a rivastigmine tartrate gel patch. (See, e.g., FIG. 3) Blood samples were drawn periodically assayed for rivastigmine.

Figure 7:
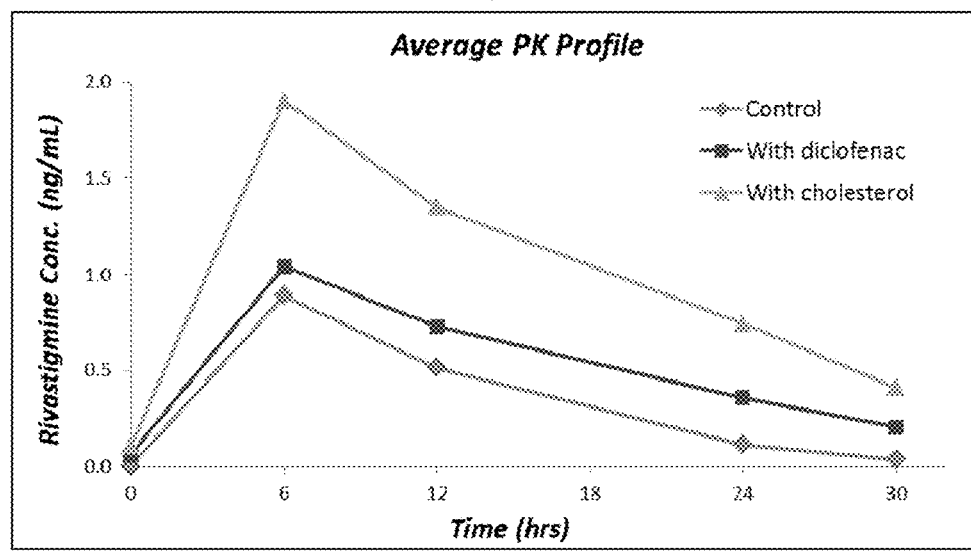
FIG. 7 illustrates the pharmacokinetics (plasma concentration) of rivastigmine using cholesterol, diclofenac, or no anti-healing compound, when tested in vivo in swine.
Figure 8:
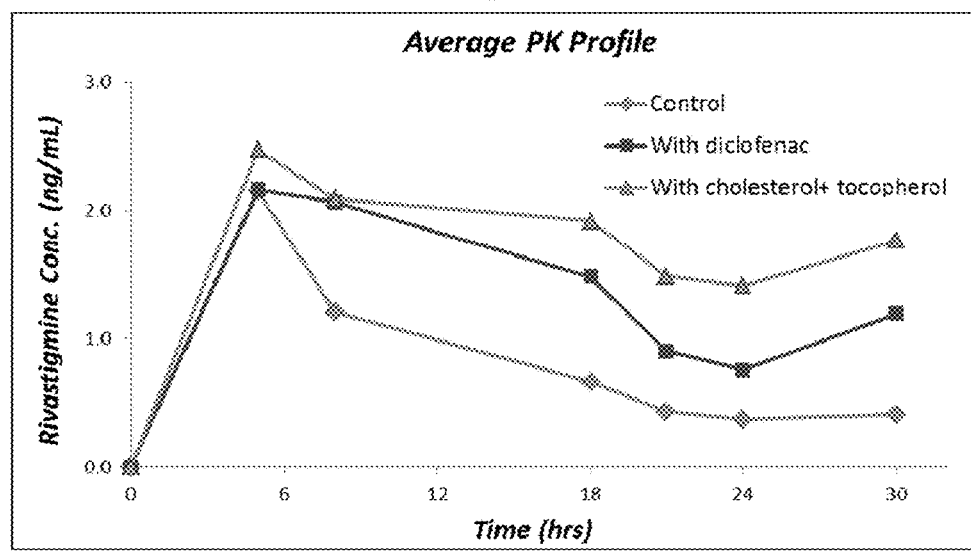
FIG. 8 illustrates the pharmacokinetics (plasma concentration) of rivastigmine using a mixture of cholesterol and tocopherol, diclofenac, or no anti-healing compound, when tested in vivo in mini-pigs.

FIG. 7 shows results for the three formulations. The results show that the cholesterol formulation exhibited enhanced drug delivery, and that the enhanced effect was sustained over the time period studied.

Example 5—In Vivo Drug Delivery

This example shows the ability of cholesterol and tocopherol to enhance in vivo drug delivery, as measured by drug plasma concentration in swine.

Plasma levels of rivastigmine were assessed in vivo in mini-pigs, using rivastigmine gel patch compositions formulated with cholesterol and tocopherol, diclofenac, or no anti-healing compound. The cholesterol+tocopherol composition included 3.4% rivastigmine, 80.3% DPG, 12.6% HPC, 1.7% cholesterol, and 2% tocopherol. The diclofenac composition included 3.4% rivastigmine, 80.6% DPG, 12.6% HPC, and 3.4% diclofenac. The gel with no anti-healing compound included 3.4% rivastigmine, 84% DPG, and 12.6% HPC. A microneedle device was inserted into the skin and removed, followed by application of a rivastigmine tartrate gel patch. (See, e.g., FIG. 3) Blood samples were drawn periodically assayed for rivastigmine.

The results showed that the cholesterol+tocopherol formulation exhibited enhanced drug delivery, and that the enhanced effect was sustained over the time period studied. The results also showed that the cholesterol+tocopherol formulation delivered significantly more drug over the time period studied, e.g., about twice that delivered by the composition with no anti-healing compound (as measured by AUC).

The foregoing description is provided for purposes of illustration and description, and is not intended to be exhaustive or to limit the invention. The invention includes all possible permutations and combinations of specific features of the embodiments described herein.

What is claimed is:

1. A method of prolonging the transdermal delivery of a drug through the skin of a subject in need thereof, comprising treating a site of the subject's skin that has been or will be treated with an active transdermal device to form microchannels in the subject's skin at the skin site with an anti-healing compound that inhibits healing of the skin to close the microchannels, wherein the anti-healing compound comprises tocopherol.

2. A method of transdermally administering a drug through the skin of a subject in need thereof, comprising:
    treating a site of the subject's skin with an active transdermal device to form microchannels in the subject's skin at the skin site;
    treating the skin site with an anti-healing compound that inhibits healing of the skin to close the microchannels; and
    transdermally administering the drug through the skin site,
    wherein the anti-healing compound comprises tocopherol.

3. The method of claim 1, wherein the anti-healing compound is applied in an amount effective to prolong the lifetime of the microchannels by at least 2 hours.

4. The method of claim 1, wherein the anti-healing compound is applied in an amount effective to prolong the lifetime of the microchannels by at least 24 hours.

5. The method of claim 1, wherein the anti-healing compound is formulated in a composition for transdermal administration.

6. The method of claim 2, wherein the active transdermal device is a microneedle device comprising an array of a plurality of microneedles.

7. The method of claim 2, wherein the drug is formulated in a flexible, finite polymeric matrix composition for transdermal administration.

8. The method of claim 6, wherein the anti-healing compound and drug are both coated on and/or incorporated into the microneedles and/or a face of the microneedle device, such that the method is effected by applying the microneedle device to the skin site.

9. The method of claim 6, wherein the anti-healing compound is coated on and/or incorporated into the microneedles and/or a face of the microneedle device, such that the method is effected by applying the microneedle device to the skin site and transdermally administering the drug through the skin site.

10. The method of claim 6, wherein the drug is coated on and/or incorporated into the microneedles and/or a face of the microneedle device, such that the method is effected by:

(a) applying the microneedle device to the skin site, and, (b) before or after step (a), treating the skin site with the anti-healing compound.

11. The method of claim 2, wherein the anti-healing compound and drug are formulated in the same composition, such that the method is effected by:

(a) treating the skin site with an active transdermal device and (b) before or after step (a), applying the composition comprising the anti-healing compound and drug to the skin site.

12. The method of claim 2, wherein anti-healing compound and drug each are provided separately from the active transdermal device, and wherein the method is effected by:

(a) treating the skin site with the active transdermal device;

(b) before or after step (a), applying a composition comprising the anti-healing compound to the skin site; and (c) after step (a) and before or after step (b), applying a composition comprising the drug to the skin site.

13. The method of claim 12, wherein:

the anti-healing compound is formulated in a solid, semi-solid, liquid, gel, ointment, cream, or emulsion composition formulated for transdermal administration;

the drug is formulated in a polymer matrix composition formulated for transdermal administration, and step (b) is carried out prior to step (c).

14. The method of claim 2, wherein the active transdermal device is selected from the group consisting of microneedle devices, radio frequency ablation devices, thermal ablation devices, chemical ablation devices, laser ablation devices, rubbing ablation devices, electroporation devices, jet injection devices, water jet devices, irradiation devices, and plasma treatment devices.

15. An active transdermal device that forms microchannels in a subject's skin having a skin-treatment side that contacts the skin during use, and comprising an anti-healing compound that inhibits healing of the skin to close the microchannels, wherein the anti-healing compound comprises tocopherol, and is coated on or incorporated into the skin-treatment side of the active transdermal device.

16. A packaged combination comprising:

(a) an active transdermal device that forms microchannels in a subject's skin having a skin-treatment side that contacts the skin during use, and comprising a drug coated on or incorporated into the skin-treatment side of the active transdermal device; and (b) a composition formulated for transdermal administration comprising an anti-healing compound that inhibits healing of the skin to close the microchannels, wherein the anti-healing compound comprises tocopherol.

17. A packaged combination comprising:

(a) an active transdermal device that forms microchannels in a subject's skin;

(b) a composition formulated for transdermal administration comprising an anti-healing compound that inhibits healing of the skin, wherein the anti-healing compound comprises tocopherol; and (c) a composition formulated for transdermal administration comprising a drug.

18. A packaged combination comprising:

(a) an active transdermal device that forms microchannels in a subject's skin having a skin-treatment side that contacts the skin during use, comprising a composition formulated for transdermal administration comprising an anti-healing compound that inhibits healing of the skin to close the microchannels, wherein the anti-healing compound comprises tocopherol, wherein the composition is coated on or incorporated into the skin-treatment side of the active transdermal device; and (b) a composition formulated for transdermal administration comprising a drug.

\* \* \* \* \*